United States Patent
Qian

(10) Patent No.: US 9,637,444 B2
(45) Date of Patent: May 2, 2017

(54) BISOXIME ESTER PHOTOINITIATOR AND PREPARATION METHOD AND USE THEREOF

(71) Applicants: Changzhou Tronly Advanced Electronic Materials Co., Ltd., Jiangsu (CN); Changzhou Tronly New Electronic Materials Co., Ltd., Jiangsu (CN)

(72) Inventor: Xiaochun Qian, Jiangsu (CN)

(73) Assignees: Changzhou Tronly Advanced Electronic Materials Co., Ltd., Jiangsu (CN); Changzhou Tronly New Electronic Materials Co., Ltd., Jiangsu (CN)

(*) Notice: Subject to any disclaimer, the term of this patent is extended or adjusted under 35 U.S.C. 154(b) by 0 days.

(21) Appl. No.: 15/116,932

(22) PCT Filed: Mar. 17, 2015

(86) PCT No.: PCT/CN2015/074360
§ 371 (c)(1),
(2) Date: Aug. 5, 2016

(87) PCT Pub. No.: WO2015/139601
PCT Pub. Date: Sep. 24, 2015

(65) Prior Publication Data
US 2016/0376226 A1 Dec. 29, 2016

(30) Foreign Application Priority Data

Mar. 18, 2014 (CN) .......................... 2014 1 0100523

(51) Int. Cl.
| | |
|---|---|
| C07C 251/66 | (2006.01) |
| C07C 319/20 | (2006.01) |
| C07D 335/12 | (2006.01) |
| C07D 409/14 | (2006.01) |
| C07C 249/04 | (2006.01) |
| C07D 311/82 | (2006.01) |
| C07D 307/91 | (2006.01) |
| C07C 323/63 | (2006.01) |
| C07D 333/76 | (2006.01) |
| C07D 409/12 | (2006.01) |
| C07D 209/86 | (2006.01) |
| C07C 323/47 | (2006.01) |

(52) U.S. Cl.
CPC .......... *C07C 251/66* (2013.01); *C07C 249/04* (2013.01); *C07C 319/20* (2013.01); *C07C 323/47* (2013.01); *C07C 323/63* (2013.01); *C07D 209/86* (2013.01); *C07D 307/91* (2013.01); *C07D 311/82* (2013.01); *C07D 333/76* (2013.01); *C07D 335/12* (2013.01); *C07D 409/12* (2013.01); *C07D 409/14* (2013.01); *C07C 2101/02* (2013.01); *C07C 2101/08* (2013.01)

(58) Field of Classification Search
None
See application file for complete search history.

(56) References Cited

FOREIGN PATENT DOCUMENTS

| | | |
|---|---|---|
| CN | 1241562 A | 1/2000 |
| CN | 101508744 A | 8/2009 |
| CN | 101565472 A | 10/2009 |
| CN | 103293855 A | 9/2013 |
| CN | 103819583 A | 5/2014 |
| CN | 103833872 A | 6/2014 |
| CN | 104076606 A | 10/2014 |
| JP | 2012093694 A | 5/2012 |
| WO | WO-02/100903 A1 | 12/2002 |
| WO | WO-2012/068879 A1 | 5/2012 |
| WO | WO-2014/121701 A1 | 8/2014 |

OTHER PUBLICATIONS

CAPLUS printout of foreign patent No. JP2008037930, published on Feb. 21, 2008.*

* cited by examiner

*Primary Examiner* — Matthew Coughlin
*Assistant Examiner* — Po-Chih Chen
(74) *Attorney, Agent, or Firm* — Cesari and McKenna LLP

(57) ABSTRACT

A bisoxime ester photoinitiator as represented by general formula (I). By introducing a bisoxime ester group and a cycloalkylalkyl group into the chemical structure, this photoinitiator not only has excellent performance in aspects of storage stability, photosensitivity, developability, pattern integrity, and the like, but also exhibits obviously improved photosensitivity and thermal stability compared to similar photoinitiators.

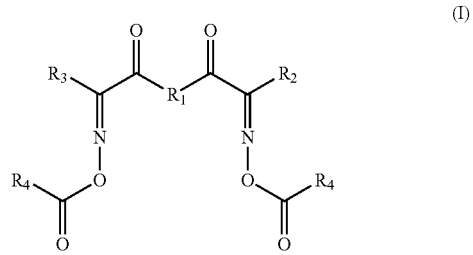

(I)

10 Claims, No Drawings

BISOXIME ESTER PHOTOINITIATOR AND PREPARATION METHOD AND USE THEREOF

CROSS REFERENCE TO RELATED APPLICATIONS

This application is the National Stage of International Application No. PCT/CN2015/074360, filed on Mar. 17, 2015, which claims priority to Chinese Application No. 201410100523.3, filed on Mar. 18, 2014. The contents of both applications are hereby incorporated by reference in their entirety.

TECHNICAL FIELD

This invention pertains to the technical field of photoinitiators, and particularly to a bisoxime ester photoinitiator and a preparation method and a use thereof.

BACKGROUND ART

The use of compounds having an oxime ester structure as photoinitiators has been well known in the art, and for example, patent documents having Publication Nos. CN1241562A, CN101508744A, CN101565472A, CN103293855A, etc., have disclosed different carbazole oxime ester photoinitiators and ketoxime ester photoinitiators. These disclosed photoinitiators can satisfy normal application requirements in the current field of photocuring such as display panels, color filters, etc., to different extents.

However, since the development of electronic technologies changes rapidly, the existing products started to exhibit deficiencies in some application fields, and the requirements for photoinitiators are higher due to replacement and upgrade of products. At present, for example, most of photoresists used for space control materials do not have good heat resistance, collapse is prone to occur in the process of baking or packaging to result in the shrinkage of space materials, whereas intended increase of the height of the space control material in the process of coating, development by exposure, or the like will result in increased cost, and small molecules melted out upon collapse due to heating will cause contamination of liquid crystal. Furthermore, for example, in the production of premium color filters, the photoinitiator has to meet basic requirements of having high solubility and good thermal stability on the one hand, and its high color quality performance requires a highly colored resist on the other hand. However, as the content of pigments increases, the curing of color resist becomes more difficult, and there are also relatively high requirements for the clarity and the integrity of images after curing. This requires an initiator having a higher photosensitivity to solve the problems described above.

In the field of photocuring, a photoinitiator, which has a high photosensitivity and a high stability and is easy to be prepared, is still the first choice in the development of this field, and the research and development of a photoinitiator having higher performances is always a key task in this field.

SUMMARY OF THE INVENTION

An object of this invention is to provide a bisoxime ester photoinitiator having excellent application performances. By introducing a bisoxime ester group into the chemical structure, this photoinitiator not only has excellent performance in aspects of storage stability, photosensitivity, developability, pattern integrity, and the like, but also exhibits obviously improved photosensitivity and thermal stability compared to similar photoinitiators.

In order to achieve the technical effect described above, a technical solution used in this invention is as follows:

a bisoxime ester photoinitiator, having a structure represented by general formula (I):

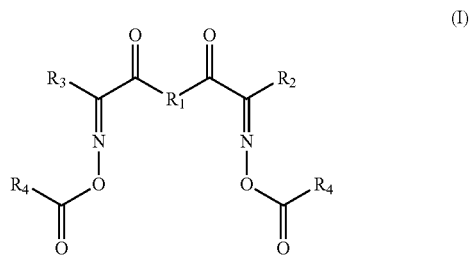

wherein,
$R_1$ is

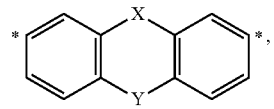

wherein * represents a binding position, and X is blank (i.e., two benzene rings on the left and on the right are connected with each other only by Y), a single bond, or a $C_1$-$C_5$ alkylene group; and Y is O, S, or a $R_5N$— group, wherein $R_5$ is hydrogen, a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group;

$R_2$ and $R_3$ each independently represents a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, and optionally, hydrogen in the above groups may be substituted with a group selected from the group consisting of halogen, a nitro group, a hydroxy group, a carboxyl group, a sulfonic acid group, an amino group, a cyano group, and an alkoxy group; provided that at least one of $R_2$ and $R_3$ is a cycloalkylalkyl group which is unsubstituted or substituted with one or more group selected from the group consisting of halogen, a nitro group, a hydroxy group, a carboxyl group, a sulfonic acid group, an amino group, a cyano group, and an alkoxy group, and the structure of said cycloalkylalkyl group is

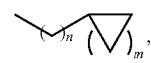

wherein n is an integer of 1-5 and m is an integer of 1-6;

$R_4$ represents a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_3$-$C_{20}$ heteroaryl group, and a $C_6$-$C_{20}$ aryl group, and optionally, hydrogen in the above groups may be substituted with a group selected from the group consisting of halogen, a phenyl group, a nitro group, a hydroxy group, a carboxyl group, a sulfonic acid group, an amino group, a cyano group, and an alkoxy group.

As a preferable option of this invention, in the bisoxime ester photoinitiator represented by the general formula (I) described above:

in $R_1$, X is blank, a single bond, a methylene group, an ethylene group, or a propylene group; and Y is O, S, or a $R_5N$— group, wherein $R_5$ is hydrogen or a $C_1$-$C_{10}$ linear or branched alkyl group;

$R_2$ and $R_3$ each independently represent a $C_1$-$C_5$ linear or branched alkyl group or a $C_4$-$C_{15}$ cycloalkylalkyl group, and optionally, hydrogen in the above groups may be substituted with a group selected from the group consisting of halogen, a nitro group, a cyano group, and an alkoxy group; provided that at least one of $R_2$ and $R_3$ is a cycloalkylalkyl group which is unsubstituted or substituted with one or more group selected from the group consisting of halogen, a nitro group, a cyano group, and an alkoxy group, and the structure of said cycloalkylalkyl group is

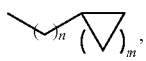

wherein n is an integer of 1-5 and m is an integer of 1-3;

$R_4$ represents a $C_1$-$C_5$ linear or branched alkyl group, a $C_3$-$C_8$ cycloalkyl group, a $C_4$-$C_8$ cycloalkylalkyl group, a $C_4$-$C_8$ alkylcycloalkyl group, a $C_3$-$C_5$ heteroaryl group, and a $C_6$-$C_{10}$ aryl group, and optionally, hydrogen in the above groups may be substituted with a group selected from the group consisting of halogen, a nitro group, and an alkoxy group.

Further preferably, $R_1$ is selected from the group consisting of the following structures:

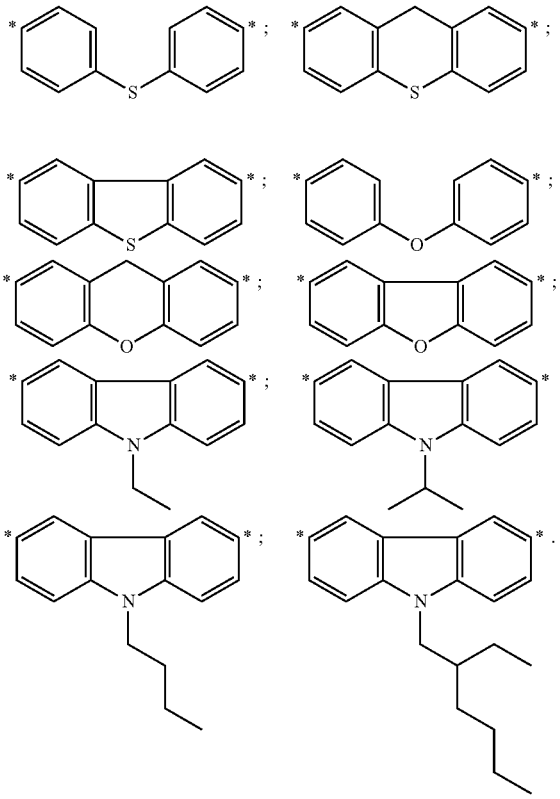

This invention also relates to a preparation method of the bisoxime ester photoinitiator represented by the general formula (I) described above, comprising the steps of:

(1) synthesis of an intermediate 1, wherein:

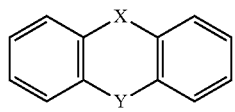

as a starting material and an acid halide compound containing a $R_2$ group and a $R_3$ group are used to synthesize the intermediate 1 through a Friedel-Crafts reaction under the action of aluminum trichloride or zinc chloride, and the reaction formula is as follows:

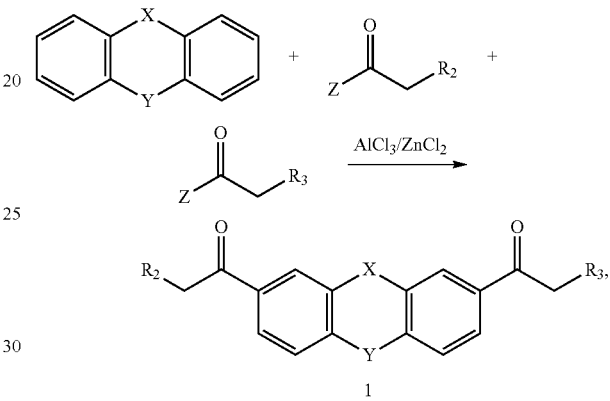

wherein Z represents halogen, such as F, Cl, Br, or I;

(2) synthesis of an intermediate 2, wherein: an oximation reaction is performed between the intermediate 1 and a nitrite ester (such as ethyl nitrite, isopentyl nitrite, isooctyl nitrite, etc.) or a nitrite salt (such as sodium nitrite, potassium nitrite, etc.) under the action of hydrogen chloride, sodium alkoxide, or potassium alkoxide to generate an intermediate 2, and the reaction formula is as follows:

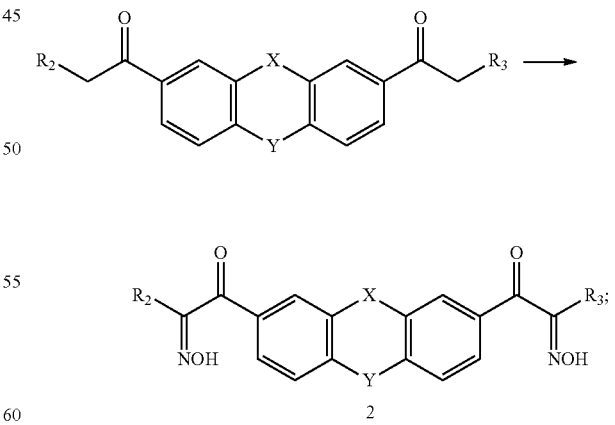

(3) synthesis of the bisoxime ester photoinitiator, wherein: an esterification reaction is performed between the intermediate 2 and an acid halide compound or an acid anhydride containing a $R_4$ group to synthesize a bisoxime ester photoinitiator product, and the reaction formula is as follows:

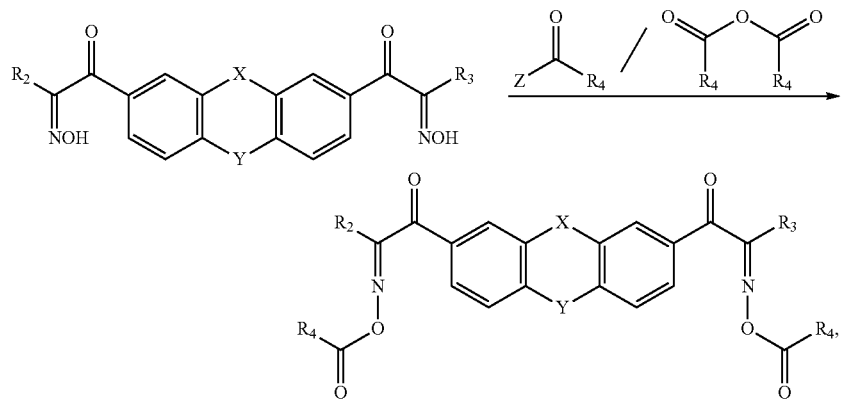

wherein Z represents halogen, such as F, Cl, Br, or I.

All of the raw materials used in the preparation method described above are compounds which are known in the prior art, commercially available, or prepared by known synthetic methods. This preparation method is simple, does not produce polluted wastes in the preparation process thereof, has high product purity, and is suitable for industrial batch production.

This invention also relates to use of the bisoxime ester photoinitiator represented by the general formula (I) described above in a photocurable composition (i.e., a photosensitive composition). Without limitation, this photoinitiator may be used in aspects such as color photoresists (RGB), black photoresists (BM), photo-spacers, dry films, semiconductor photoresists, inks, etc.

DESCRIPTION OF EMBODIMENTS

Hereafter, this invention will be further illustrated in conjunction with specific Examples, but it is not to be understood that the scope of this invention is limited thereto.

PREPARATION EXAMPLE

Example 1

Preparation of bis-{[4-(3-cyclopentyl-1,2-dione-2-oxime-O-propionate)propyl]phenylene}-sulfide (compound 1)

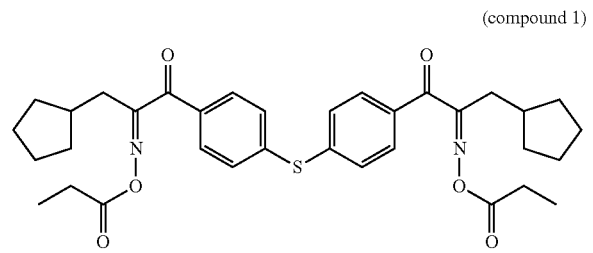 [SMILES: CCC(=O)ON=C(CC1CCCC1)C(=O)c1ccc(Sc2ccc(C(=O)C(CC3CCCC3)=NOC(=O)CC)cc2)cc1]

Step (1): preparation of bis-{[4-(3-cyclopentyl-1-one)propyl]phenylene}-sulfide

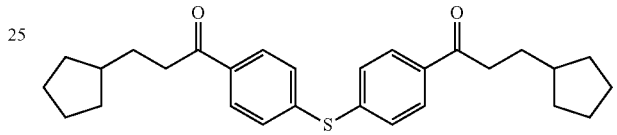

18.6 g of diphenyl sulfide, 29.4 g of AlCl$_3$ (finely ground), and 100 mL of dichloromethane were charged into a 500 mL four-neck flask, stirred, and cooled in an ice bath. When the temperature decreased to 0° C., a mixed liquid of 33.7 g of cyclopentylpropionyl chloride and 50 g of dichloromethane were begun to be dropped for about 1.5 h with the temperature being controlled at 10° C. or less, stirring was continued for 2 h, and then the reaction was stopped. The reaction liquid was poured into a diluted hydrochloric acid formulated with 400 g of ice and 65 mL of concentrated hydrochloric acid, the liquid in the lower layer was separated using a separation funnel, and the upper layer was extracted with 50 mL of dichloromethane. The extract and the liquid were combined with each other, washed with a NaHCO$_3$ solution formulated with 10 g of NaHCO$_3$ and 200 g of water, and were further washed with 200 mL of water for 3 times until pH value become neutral. Water was removed by drying with 30 g of anhydrous MgSO$_4$, and dichloromethane was evaporated by rotation. After evaporation, the crude product in a rotary evaporation flask presented the form of light yellow liquid and was poured into 200 mL of petroleum ether evaporated under normal pressure to obtain a white powdery solid upon stirring and suction filtration, and a product of 39.1 g was obtained after drying in an oven at 50° C. for 5 h, with a yield of 90% and a purity of 96.2%.

The structure of the product in step (1) was determined by hydrogen nuclear magnetic resonance spectroscopy, and the specific characteristic result is as follows:

$^1$H-NMR(CDCl$_3$, 500 MHz): 1.4274-1.5412 (22H, m), 2.5214-2.6276 (4H, t), 7.2738-7.3818 (4H, d), 7.7908-7.9824 (4H, d).

Step (2): preparation of bis-{[4-(3-cyclopentyl-1,2-dione-2-oxime)propyl]phenylene}-sulfide

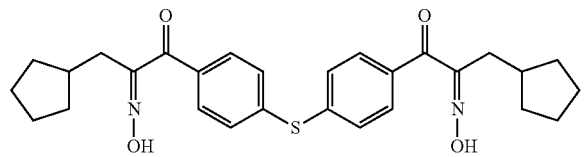 [SMILES: O=C(C(CC1CCCC1)=NO)c1ccc(Sc2ccc(C(=O)C(CC3CCCC3)=NO)cc2)cc1]

21.7 g of the product of step (1), 100 mL of tetrahydrofuran, 13.2 g of concentrated hydrochloric acid, and 11.8 g of isopentyl nitrite were added into a 250 mL four-neck flask, stirred at normal temperature for 5 h, and then the reaction was stopped. Materials were poured into a 2000 mL large beaker and stirred after 1000 mL of water was added, and 200 g of dichloromethane was used for extraction. The extract was dried by adding 50 g of anhydrous $MgSO_4$, followed by suction filtration. The solvent was removed by rotary evaporation of the filtrate under reduced pressure, and an oily viscous matter was obtained in a rotary bottle. The viscous matter was poured into 150 mL of petroleum ether and was precipitated with stirring, followed by suction filtration, a white powdery solid was obtained, and after drying at 60° C. for 5 h, a product of 20.9 g was obtained with a yield of 85% and a relative purity of 95.2%.

The structure of the product in step (2) was determined by hydrogen nuclear magnetic resonance spectroscopy, and the specific characteristic result is as follows:

$^1$H-NMR(CDCl$_3$, 500 MHz): 1.4037-1.5431 (18H, m), 2.0321-2.1735 (2H, s), 2.5001-2.7221 (4H, d), 7.3034-7.3241 (4H, d), 7.8002-7.9922 (4H, m).

Step (3): preparation of bis-{[4-(3-cyclopentyl-1,2-dione-2-oxime-O-propionate) propyl]phenylene}-sulfide 19.7 g of the product of step (2), 100 g of dichloromethane, and 4.1 g of triethylamine were added into a 250 mL four-neck flask and were stirred at room temperature for 5 min, and then 7.8 g of propionyl chloride was dropped within about 30 min. Stirring was continued for 2 h, and then 5% NaHCO$_3$ aqueous solution was added to adjust pH value to become neutral. An organic layer was separated with a separation funnel, followed by washing twice with 200 mL of water and drying with 50 g of anhydrous MgSO$_4$, and the solvent was evaporated by rotation to obtain a viscous liquid. Recrystallization with methanol obtained a white solid powder, which was filtered to obtain a product of 23.1 g with a purity of 99%.

The structure of the final product was determined by hydrogen nuclear magnetic resonance spectroscopy, and the specific characteristic result is as follows:

$^1$H-NMR(CDCl$_3$, 500 MHz): 0.9351-1.1213 (6H, t), 1.3351-1.4913 (18H, m), 2.1737-2.2923 (4H, m), 2.6981-2.8821 (4H, m), 7.3201-8.1241 (8H, d).

Example 2

Preparation of [2-(3-cyclopropyl-1,2-dione-2-oxime-O-propionate)propyl]-[7-(4-cyclopentyl-1,2-dione-2-oxime-O-propionate)butyl]-thioxanthene (compound 2)

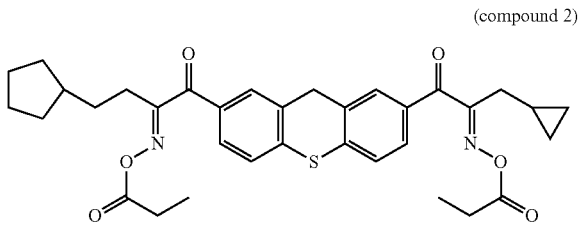 [SMILES: CCC(=O)O/N=C(\CCC1CCCC1)C(=O)c1ccc2c(c1)Cc1cc(C(=O)/C(CC3CC3)=N/OC(=O)CC)ccc1S2]

Step (1): preparation of [2-(3-cyclopropyl-1-one)propyl]-[7-(4-cyclopentyl-1-one)butyl]-thioxanthene

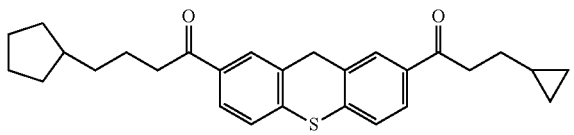 [SMILES: O=C(CCCC1CCCC1)c1ccc2c(c1)Cc1cc(C(=O)CCC3CC3)ccc1S2]

19.8 g of thioxanthene, 14.7 g of AlCl$_3$ (finely ground), and 100 mL of dichloromethane were charged into a 500 mL four-neck flask, stirred, and cooled in an ice bath. When the temperature decreased to 0° C., a mixed liquid of 13.5 g of cyclopropylpropionyl chloride and 25 g of dichloromethane were begun to be dropped for about 1.5 h with the temperature being controlled at 10° C. or less, and stirring was continued for 2 h. 14.7 g of AlCl$_3$ (finely ground) was then added into the four-neck flask, a mixed liquid of 17.8 g of cyclopentylbutanoyl chloride and 25 g of dichloromethane was dropped for about 1.5 h with the temperature being controlled at 10° C. or less, the temperature was raised to 15° C., stirring was continued for 2 h, and then the reaction was stopped. The reaction liquid was poured into diluted hydrochloric acid formulated with 400 g of ice and 65 mL of concentrated hydrochloric acid, the liquid in the lower layer was separated using a separation funnel, and the upper layer was extracted with 50 mL of dichloromethane. The extract and the liquid were combined with each other, washed with NaHCO$_3$ solution formulated with 10 g of NaHCO$_3$ and 200 g of water, and were further washed with 200 mL of water for 3 times until pH value become neutral. Water was removed by drying with 30 g of anhydrous MgSO$_4$, and dichloromethane was evaporated by rotation. After evaporation, the crude product in a rotary evaporation flask presented the form of light yellow liquid and was poured into 200 mL of petroleum ether evaporated under normal pressure to obtain a white powdery solid upon stirring and suction filtration, and a product of 38.1 g was obtained after drying in an oven at 50° C. for 5 h, with a yield of 88% and a purity of 96.2%.

The structure of the product in step (1) was determined by hydrogen nuclear magnetic resonance spectroscopy, and the specific characteristic result is as follows:

¹H-NMR(CDCl₃, 500 MHz): 0.19366-0.2114 (5H, m), 1.2744-1.5831 (15H, m), 2.5762-2.6144 (4H, t), 3.7659-3.8407 (2H, s), 7.1908-7.2824 (2H, d), 7.4457-7.5763 (4H, m).

Step (2): preparation of [2-(3-cyclopropyl-1,2-dione-2-oxime)propyl]-[7-(4-cyclopentyl-1,2-dione-2-oxime)butyl]-thioxanthene

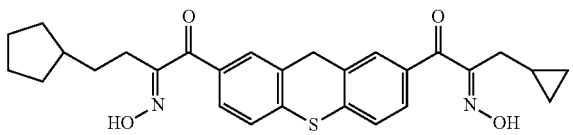 [SMILES: O=C(/C(CCC1CCCC1)=N/O)c1ccc2c(c1)Cc1cc(C(=O)/C(CC3CC3)=N/O)ccc1S2]

21.6 g of the product of step (1), 100 mL of tetrahydrofuran, 13.2 g of concentrated hydrochloric acid, and 11.8 g of isopentyl nitrite were added into a 250 mL four-neck flask, stirred at normal temperature for 5 h, and then the reaction was stopped. Materials were poured into a 2000 mL large beaker and stirred after 1000 mL of water was added, and 200 g of dichloromethane was used for extraction. The extract was dried by adding 50 g of anhydrous MgSO₄, followed by suction filtration. The filtrate was removed by rotary evaporation under reduced pressure, and an oily viscous matter was obtained in a rotary bottle. The viscous matter was poured into 150 mL of petroleum ether and was precipitated with stirring, followed by suction filtration, a white powdery solid was obtained, and after drying at 60° C. for 5 h, a product of 21.1 g was obtained with a yield of 86% and a relative purity of 95.2%.

The structure of the product in step (2) was determined by hydrogen nuclear magnetic resonance spectroscopy, and the specific characteristic result is as follows:

1H-NMR(CDCl₃, 500 MHz): 0.2037-0.2431 (5H, m), 1.4355-1.5032 (11H, m), 2.0117-2.1349 (2H, s), 2.5132-2.7065 (4H, m), 3.8002 (2H, s), 7.3034-7.5241 (6H, d).

Step (3): preparation of [2-(3-cyclopropyl-1,2-dione-2-oxime-O-propionate) propyl]-[7-(4-cyclopentyl-1,2-dione-2-oxime-O-propionate) butyl]-thioxanthene 19.6 g of the product of step (2), 100 g of dichloromethane, and 4.1 g of triethylamine were added into a 250 ml four-neck flask and were stirred at room temperature for 5 min, and then 7.6 g of propionyl chloride was dropped within about 30 min. Stirring was continued for 2 h, and then 5% NaHCO₃ aqueous solution was added to adjust pH value to become neutral. An organic layer was separated with a separation funnel, followed by washing twice with 200 mL of water and drying with 50 g of anhydrous MgSO₄, and the solvent was evaporated by rotation to obtain a viscous liquid. Recrystallization with methanol obtained a white solid powder, which was filtered to obtain a product of 22.1 g with a purity of 99%.

The structure of the final product was determined by hydrogen nuclear magnetic resonance spectroscopy, and the specific characteristic result is as follows:

¹H-NMR(CDCl₃, 500 MHz): 0.1981-0.2209 (5H, m), 1.1038-1.2004 (6H, m), 1.498-1.5703 (11H, m), 2.2765-2.3951 (4H, m), 2.5964-2.7123 (4H, m), 3.8678 (2H, s), 7.2854-7.3409 (2H, d), 7.3988-7.5028 (4H, m).

Examples 3-13

Referring to the method illustrated in Example 1 or 2, compounds shown in Examples 3-13 were prepared from

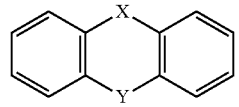

and corresponding acylating agents.

The structures of compounds of interest and ¹H-NMR data thereof were listed in Table 1.

TABLE 1

| Examples | Compounds (3-13) | ¹H NMR δ[ppm] |
|---|---|---|
| Example 3 | Compound 3 | 0.1771-0.2134(5H, m)<br>2.2191-2.2721(6H, s)<br>2.3176-2.4481(2H, d)<br>3.0211-3.3113(2H, s)<br>7.2853-7.9062(8H, d) |
| Example 4 | Compound 4 | 0.1801-0.2068(5H, m)<br>1.1067-1.2024(6H, s)<br>1.4431-1.5199(11H, m)<br>2.3308-2.4542(4H, m)<br>2.7150-2.8604(4H, t)<br>7.2743-8.0032(8H, m) |

TABLE 1-continued
| Examples | Compounds (3-13) | ¹H NMR δ[ppm] |
|---|---|---|
| Example 5 | 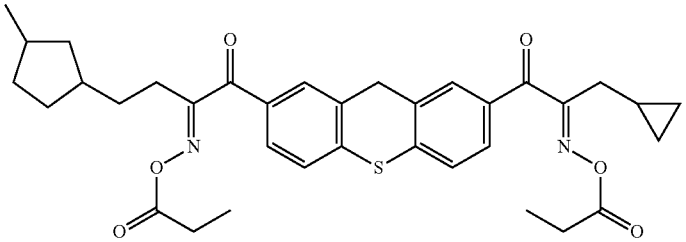<br>Compound 5 | 0.1799-0.2134(5H, m)<br>1.0056-1.1387(9H, m)<br>1.4500-1.6583(10H, m)<br>2.2165-2.3566(4H, s)<br>2.7381-2.8436(4H, t)<br>3.8655(2H, s)<br>7.2433-7.5741(6H, m) |
| Example 6 | 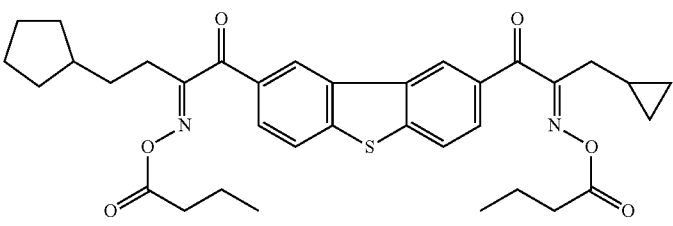<br>Compound 6 | 0.1801-0.2104(5H, m)<br>0.9560-1.0801(6H, t)<br>1.4991-1.6630(13H, m)<br>2.2001-2.3708(4H, m)<br>2.6754-2.8318(4H, m)<br>7.3093-8.1061(6H, m) |
| Example 7 | 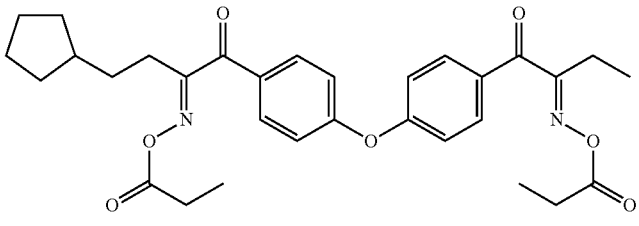<br>Compound 7 | 1.0016-1.1023(9H, t)<br>1.4128-1.5319(11H, m)<br>2.2100-2.3106(4H, m)<br>2.6128-2.8012(4H, m)<br>7.2098-7.9531(8H, m) |
| Example 8 | 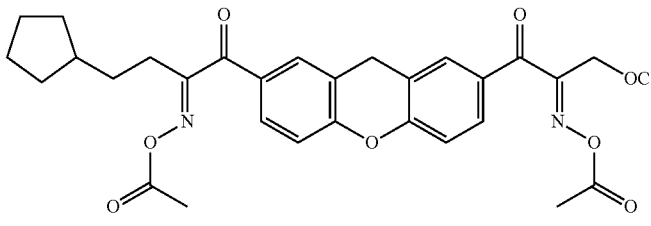<br>Compound 8 | 1.3921-1.5129(11H, m)<br>2.0309-2.2237(6H, s)<br>2.5998-2.6879(2H, t)<br>3.2231-3.2456(3H, s)<br>3.4002-3.5023(2H, s)<br>3.8001-3.9123(2H, s)<br>6.9618-7.7239(6H, m) |
| Example 9 | 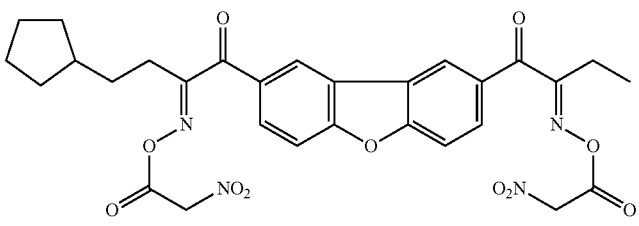<br>Compound 9 | 1.0239-1.1123(3H, t)<br>1.3906-1.5248(11H, m)<br>2.6540-2.8761(H, m)<br>5.3501-5.3501(H, s)<br>7.6681-8.2871(6H, m) |

TABLE 1-continued
| Examples | Compounds (3-13) | $^1$H NMR δ[ppm] |
|---|---|---|
| Example 10 | 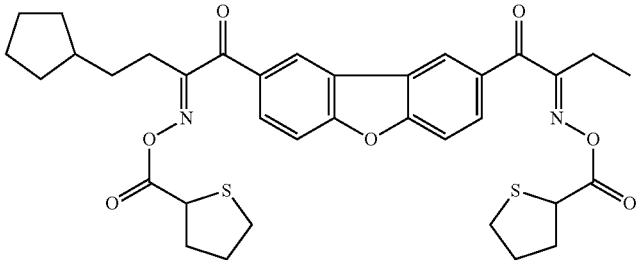<br>Compound 10 | 0.9981-1.1031(3H, t)<br>1.3909-1.5216(11H, m)<br>2.1659-2.8192(16H, m)<br>3.5602-3.9768(2H, t)<br>7.3982-8.0007(6H, m) |
| Example 11 | 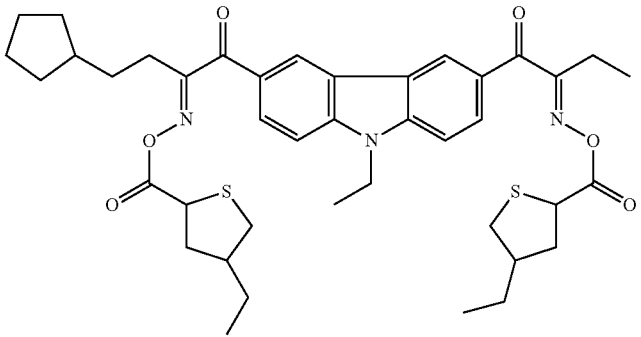<br>Compound 11 | 0.9567-1.0389(9H, t)<br>1.2908-1.5345(18H, m)<br>1.8665-2.0954(2H, m)<br>2.1981-2.3041(4H, s)<br>2.6260-2.7893(8H, m)<br>3.6782-3.93348(4H, m)<br>7.5562-8.1008(6H, m) |
| Example 12 | 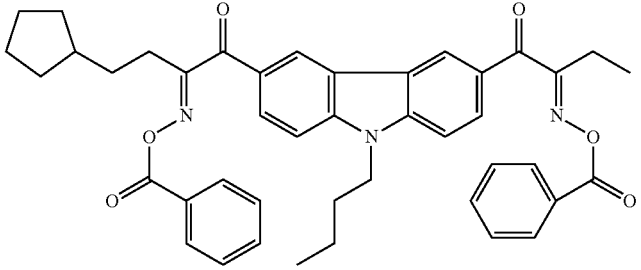<br>Compound 12 | 0.9217-1.1129(6H, t)<br>1.3781-1.7961(15H, m)<br>2.6981-2.8045(4H, m)<br>3.8109-3.9861(2H, m)<br>7.4723-8.4018(16H, m) |
| Example 13 | 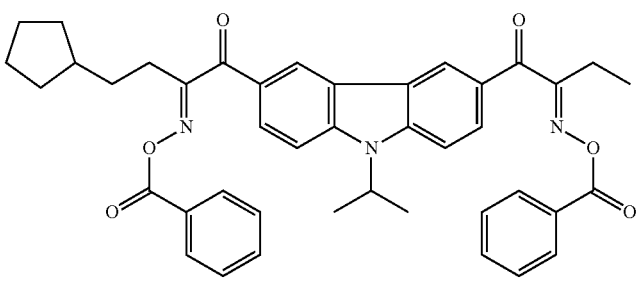<br>Compound 13 | 0.9549-1.0036(3H, t)<br>1.4029-1.5632(17H, m)<br>2.6102-2.8982(4H, m)<br>3.9651-4.1071(1H, m)<br>7.3031-8.4089(16H, m) |

Performance Evaluation

By formulating exemplary photocurable compositions, respective application performances of the photoinitiators represented by the general formula (I) of this invention, were evaluated, including aspects of storage stability, photosensitivity, developability, pattern integrity, thermal stability, etc.

1. Formulation of Photocurable Compositions
(1) Uncolored Photocurable Composition A

| | |
|---|---|
| Acrylate copolymer (Benzyl methacrylate/methacrylic acid/hydroxyethyl methacrylate (molar ratio of 70/10/20) copolymer (Mw: 10,000)) | 100 |
| Trimethylolpropane triacrylate (TMPTA) | 100 |
| Photoinitiator | 2 |
| Butanone (solvent) | 25 |

(2) Colored Photocurable Composition B

| | |
|---|---|
| Acrylate copolymer (Benzyl methacrylate/methacrylic acid/methyl methacrylate (molar ratio of 50/15/30) copolymer (Mw: 15,000)) | 100 |
| Dipentaerythritol hexaacrylate | 100 |
| Photoinitiator | 2 |
| Butanone (solvent) | 25 |
| Dye blue 15 | 5 |

In the compositions A and B described above, the photoinitiator was a bisoxime ester compound represented by the general formula (I) disclosed by this invention or a photoinitiator known in the prior art as a comparison, and the respective components were represented in parts by mass.

2. Development by Exposure

The photocurable compositions A and B described above were stirred, respectively, under protection from light. Materials were taken on a PET template and film coating was performed with a wire bar, the solvent was removed by drying at 90° C. for 5 min, and a coating film with a film thickness of about 2 μm was formed. The substrate on which the coating film was formed was cooled to room temperature, a mask plate was attached thereon, and a long wavelength irradiation was achieved with a high pressure mercury lamp 1PCS light source through a FWHM color filter. Exposure was performed on the coating film through a seam of the mask plate under an ultraviolet having a wavelength of 370-420 nm. Subsequently, development was performed by soaking in a 2.5% sodium carbonate solution at 25° C. for 20 s, followed by washing with ultra-pure water and air drying. The pattern was fixed by hard baking at 220° C. for 30 min, and the obtained pattern was evaluated.

3. Performance Evaluation of Photocurable Compositions
(1) Storage Stability

After naturally storing a liquid-state photocurable composition at room temperature for 1 month, the degree of precipitation of substances was visually evaluated according to the following criteria:

A: No precipitation was observed;
B: Precipitation was slightly observed;
C: Significant precipitation was observed.

(2) Photosensitivity

Upon exposure, the minimum exposure amount of the irradiated region having a residual film rate of 90% or more after development in the step of exposure was evaluated as the demand of exposure. A smaller exposure demand represents a higher sensitivity.

(3) Developability and Pattern Integrity

The pattern on the substrate was observed using a scanning electron microscope (SEM) to evaluate the developability and the pattern integrity.

The developability was evaluated according to the following criteria:

○: No residue was observed in unexposed portions;
◉: A small amount of residue was observed in unexposed portions, but the residue is acceptable;
●: Significant residue was observed in unexposed portions.

The pattern integrity was evaluated according to the following criteria:

◇: No pattern defects were observed;
□: A few defects were observed in some portions of the pattern;
◆: A number of defects were significantly observed in the pattern.

(4) Thermal Stability

The change of the film thickness before and after hard baking was measured using a thickness measurer to evaluate the thermal stability of the material.

Evaluation results were as shown in Table 2 and Table 3:

TABLE 2

| | | | | | | | | |
|---|---|---|---|---|---|---|---|---|
| | | | Photocurable composition A | | | | | |
| | Photoinitiator | Storage stability | Demand of exposure mJ/cm$^2$ | Developability | Pattern integrity | Thickness before hard baking | Thickness after hard baking | Change of film thickness |
| Example | Compound 1 | A | 55 | ○ | ◇ | 2.1 | 2.0 | 4.8% |
| | Compound 3 | A | 53 | ○ | ◇ | 2.0 | 1.9 | 5% |
| | Compound 5 | A | 51 | ○ | ◇ | 2.0 | 1.9 | 5% |
| | Compound 10 | A | 48 | ○ | ◇ | 1.9 | 1.8 | 5.2% |
| | Compound 12 | A | 40 | ○ | ◇ | 2.1 | 2.0 | 4.8% |
| | Compound 13 | A | 32 | ○ | ◇ | 2.0 | 1.9 | 5% |
| Comparative Example | PBG-304 | A | 70 | ◉ | □ | 2.0 | 1.7 | 15% |
| | OXE-01 | B | 105 | ◉ | ◆ | 2.0 | 1.6 | 20% |
| | OXE-02 | B | 85 | ◉ | ◆ | 2.0 | 1.6 | 20% |
| | Irgacure907 | C | 160 | ● | ◆ | 2.1 | 1.4 | 33% |

TABLE 3

| | | | Photocurable composition B | | | | | |
|---|---|---|---|---|---|---|---|---|
| | Photoinitiator | Storage stability | Demand of exposure mJ/cm$^2$ | Developability | Pattern integrity | Thickness before hard baking | Thickness after hard baking | Change of film thickness |
| Example | Compound 1 | A | 60 | ○ | ◇ | 2.0 | 1.9 | 5% |
| | Compound 3 | A | 58 | ○ | ◇ | 2.0 | 1.9 | 5% |
| | Compound 5 | A | 56 | ○ | ◇ | 2.1 | 2.0 | 4.8% |
| | Compound 10 | A | 53 | ○ | ◇ | 2.0 | 1.9 | 5% |
| | Compound 12 | A | 46 | ○ | ◇ | 2.1 | 2.0 | 4.8% |
| | Compound 13 | A | 40 | ○ | ◇ | 2.0 | 1.9 | 5% |
| Comparative Example | PBG-304 | A | 88 | ◉ | □ | 2.1 | 1.9 | 9.5% |
| | OXE-01 | B | 117 | ◉ | ◆ | 1.9 | 1.6 | 21% |
| | OXE-02 | B | 98 | ◉ | ◆ | 2.0 | 1.8 | 10% |
| | Irgacure907 | C | 176 | ● | ◆ | 2.1 | 1.6 | 24% |

In Table 2 and Table 3, PBG-304 represents a photoinitiator, 1-(6-o-methylbenzoyl-9-ethylcarbazol-3-yl)-(3-cyclopentylacetone)-1-oxime-acetate, disclosed in CN101508744A; OXE-01 represents 1-(4-phenylthio-phenyl)-octan-1,2-dione-2-oxime-O-benzoate; OXE-02 represents 1-(6-o-methylbenzoyl-9-ethylcarbazol-3-yl)-(3-ethanone)-1-oxime-acetate; and Irgacure907 represents 2-methyl-1-(4-methylthiophenyl)-2-morpholinyl-propane-1-one.

It can be seen from the results of Table 2 and Table 3 that the photocurable composition comprising the bisoxime ester photoinitiator represented by the general formula (I) of this invention has good storage stability, exhibits extremely good photosensitivity, developability, and pattern integrity in both colorless systems and pigment systems, and has a thermal stability obviously superior to those of existing photoinitiators. By comparison, there are significant shortages for PBG-304, OXE-01, OXE-02, and Irgacure 907 in aspects of storage stability, photosensitivity, developability, pattern integrity, and thermal stability.

In summary, the bisoxime ester photoinitiator represented by the general formula (I) disclosed by this invention has excellent application performances, and can greatly improve the performances of photocured products when used in photocurable compositions.

The invention claimed is:

1. A bisoxime ester photoinitiator having a structure represented by general formula (I):

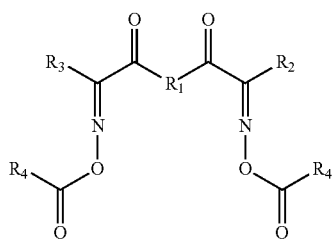

wherein
R$_1$ is

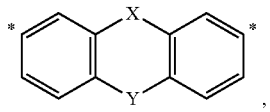

in which * represents a binding position, and X is blank, a single bond, or a C$_1$-C$_5$ alkylene group; and Y is O, S, or a R$_5$N— group, wherein R$_5$ is hydrogen, a C$_1$-C$_{20}$ linear or branched alkyl group, a C$_3$-C$_{20}$ cycloalkyl group, a C$_4$-C$_{20}$ cycloalkylalkyl group, or a C$_4$-C$_{20}$ alkylcycloalkyl group;

R$_2$ and R$_3$ each independently represent a C$_1$-C$_{20}$ linear or branched alkyl group, a C$_3$-C$_{20}$ cycloalkyl group, a C$_4$-C$_{20}$ cycloalkylalkyl group, a C$_4$-C$_{20}$ alkylcycloalkyl group, and optionally, hydrogen in the above groups may be substituted with a group selected from the group consisting of halogen, a nitro group, a hydroxy group, a carboxyl group, a sulfonic acid group, an amino group, a cyano group, and an alkoxy group; provided that at least one of R$_2$ and R$_3$ is a cycloalkylalkyl group which is unsubstituted or substituted with one or more group selected from the group consisting of halogen, a nitro group, a hydroxy group, a carboxyl group, a sulfonic acid group, an amino group, a cyano group, and an alkoxy group, and the structure of said cycloalkylalkyl group is

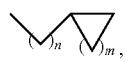

wherein n is an integer of 1-5 and m is an integer of 1-6;

R$_4$ represents a C$_1$-C$_{20}$ linear or branched alkyl group, a C$_3$-C$_{20}$ cycloalkyl group, a C$_4$-C$_{20}$ cycloalkylalkyl group, a C$_4$-C$_{20}$ alkylcycloalkyl group, a C$_3$-C$_{20}$ heteroaryl group, and a C$_6$-C$_{20}$ aryl group, and optionally, hydrogen in the above groups may be substituted with a group selected from the group consisting of halogen, a phenyl group, a nitro group, a hydroxy group, a carboxyl group, a sulfonic acid group, an amino group, a cyano group, and an alkoxy group.

2. The bisoxime ester photoinitiator according to claim 1, wherein in R$_1$, X is blank, a single bond, a methylene group, an ethylene group, or a propylene group; and Y is O, S, or a R$_5$N— group, wherein R$_5$ is hydrogen or a C$_1$-C$_{10}$ linear or branched alkyl group.

3. The bisoxime ester photoinitiator according to claim 1, wherein $R_2$ and $R_3$ each independently represents a $C_1$-$C_5$ linear or branched alkyl group or a $C_4$-$C_{15}$ cycloalkylalkyl group, and optionally, hydrogen in the above groups may be substituted with a group selected from the group consisting of halogen, a nitro group, a cyano group, and an alkoxy group; provided that at least one of $R_2$ and $R_3$ is a cycloalkylalkyl group which is unsubstituted or substituted with one or more group selected from the group consisting of halogen, a nitro group, a cyano group, and an alkoxy group, and the structure of said cycloalkylalkyl group is

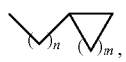

wherein n is an integer of 1-5 and m is an integer of 1-3.

4. The bisoxime ester photoinitiator according to claim 1, wherein $R_4$ represents a $C_1$-$C_5$ linear or branched alkyl group, a $C_3$-$C_8$ cycloalkyl group, a $C_4$-$C_8$ cycloalkylalkyl group, a $C_4$-$C_8$ alkylcycloalkyl group, a $C_3$-$C_5$ heteroaryl group, and a $C_6$-$C_{10}$ aryl group, and optionally, hydrogen in the above groups may be substituted with a group selected from the group consisting of halogen, a nitro group, and an alkoxy group.

5. The bisoxime ester photoinitiator according to claim 1, wherein $R_1$ is selected from the group consisting of the following structures:

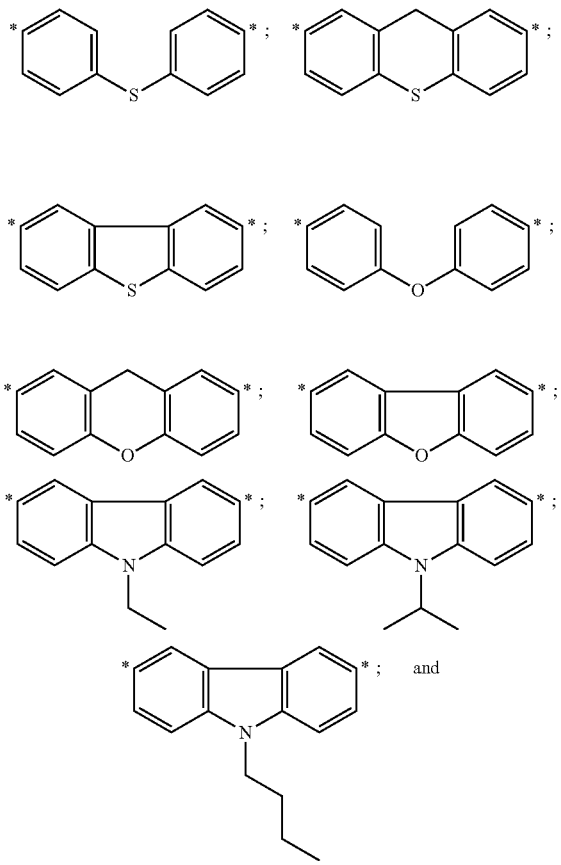

6. A preparation method of the bisoxime ester photoinitiator according to claim 1, comprising the steps of:
(1) synthesis of an intermediate 1, wherein

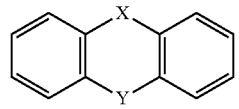

as a starting material and an acid halide compound containing a $R_2$ group and a $R_3$ group are used to synthesize the intermediate 1 through a Friedel-Crafts reaction under the action of aluminum trichloride or zinc chloride, the reaction shown as follows:

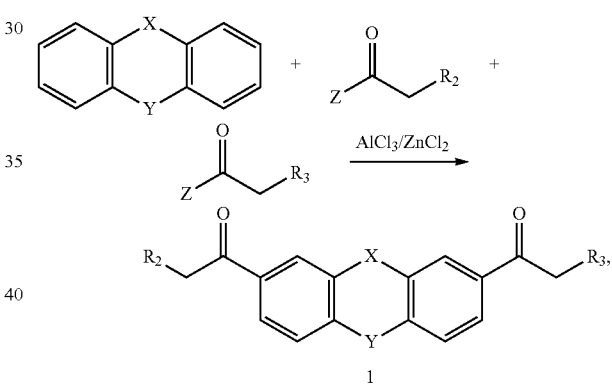

wherein Z represents halogen;
(2) synthesis of an intermediate 2, wherein an oximation reaction is performed between the intermediate 1 and a nitrite ester or a nitrite salt under the action of hydrogen chloride, sodium alkoxide, or potassium alkoxide to generate an intermediate 2, the reaction shown as follows:

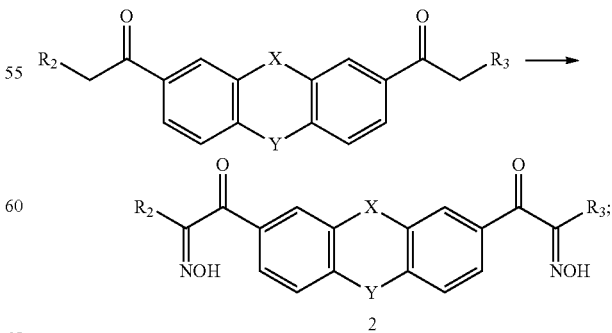

and (3) synthesis of the bisoxime ester photoinitiator, wherein an esterification reaction is performed between the intermediate 2 and an acid halide compound or an acid anhydride containing a $R_4$ group to synthesize a bisoxime ester photoinitiator product, the reaction shown as follows:

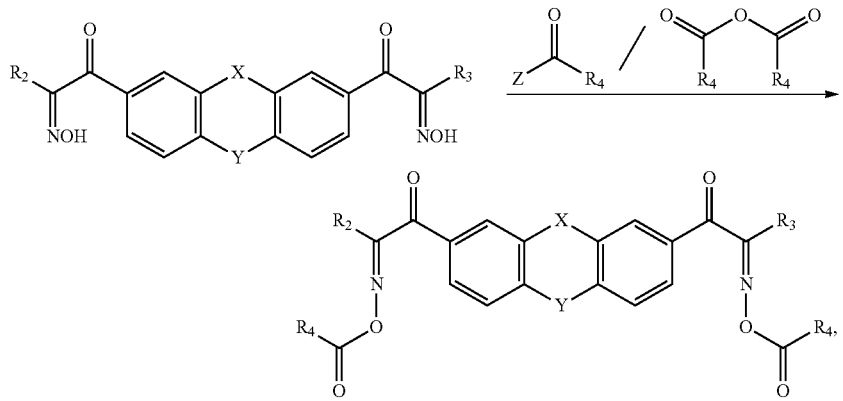

wherein Z represents halogen.

7. The preparation method according to claim 6, wherein said Z is selected from the group consisting of F, Cl, Br, or I.

8. The preparation method according to claim 6, wherein the nitrite ester is selected from the group consisting of ethyl nitrite, isopentyl nitrite, or isooctyl nitrite, and the nitrite salt is selected from the group consisting of sodium nitrite or potassium nitrite.

9. The preparation method according to claim 8, wherein the oximation reaction is performed between the intermediate 1 and the nitrite ester.

10. The preparation method according to claim 8, wherein the oximation reaction is performed between the intermediate 1 and the nitrite salt.

* * * * *